US00PP32208P2

(12) United States Plant Patent
Koppe

(10) Patent No.: US PP32,208 P2
(45) Date of Patent: Sep. 15, 2020

(54) *BEGONIA* PLANT NAMED 'KROUTRE01'

(50) Latin Name: ***Begonia boliviensis* x *Begonia* x *tuberhybrida***
Varietal Denomination: KROUTRE01

(71) Applicant: Lubbertus H. Koppe, Putten (NL)

(72) Inventor: Lubbertus H. Koppe, Putten (NL)

(73) Assignee: KOPPE ROYALTY B.V., Putten (NL)

( * ) Notice: Subject to any disclaimer, the term of this patent is extended or adjusted under 35 U.S.C. 154(b) by 0 days.

(21) Appl. No.: 16/602,490

(22) Filed: Oct. 17, 2019

(51) Int. Cl.
*A01H 5/02* (2018.01)
*A01H 6/18* (2018.01)

(52) U.S. Cl.
USPC ..... Plt./343
CPC ..... *A01H 6/18* (2018.05)

(58) Field of Classification Search
USPC ..... Plt./343
CPC ..... A01H 5/02
See application file for complete search history.

(56) References Cited

PUBLICATIONS

PLUTO UPOVROM Plant Variety Database Citation for 'Kroutre01' as per QZ PBR 20183100; Feb. 16, 2019; 1 page.*

* cited by examiner

*Primary Examiner* — Kent L Bell
(74) *Attorney, Agent, or Firm* — C. A. Whealy

(57) ABSTRACT

A new and distinct cultivar of *Begonia* plant named 'KROUTRE01', characterized by its broadly upright and mounded plant habit; moderately vigorous growth habit; moderately freely branching habit; dark greyed green-colored leaves; large single-type red-colored flowers that are positioned above and beyond the foliar plane; and continuous flowering throughout the summer.

2 Drawing Sheets

Figure 1:
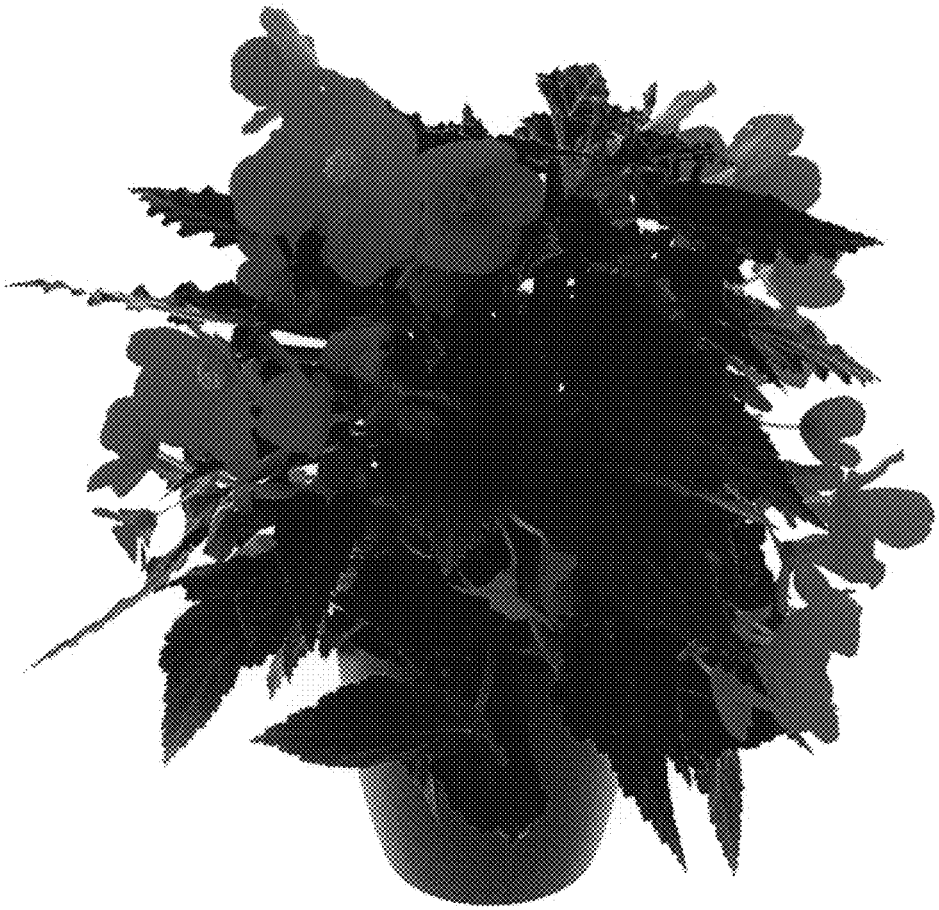

Botanical designation: *Begonia boliviensis* x *Begonia* x *tuberhybrida*.

Cultivar denomination: 'KROUTRE01'.

BACKGROUND OF THE INVENTION

The present invention relates to a new and distinct cultivar of *Begonia* plant, botanically known as *Begonia boliviensis* x *Begonia* x *tuberhybrida* and hereinafter referred to by the name 'KROUTRE01'.

The new *Begonia* plant is a product of a planned breeding program conducted by the Inventor in Ermelo, The Netherlands. The objective of the breeding program is to create new *Begonia* plants with uniform plant habit and numerous attractive flowers.

The new *Begonia* plant originated from a cross-pollination made by the Inventor in Ermelo, The Netherlands in September, 2014 of a proprietary selection of *Begonia boliviensis* identified as code number KV13H1260-004, not patented, as the female, or seed, parent with *Begonia* x *tuberhybrida* 'Nonstop Mocca', not patented, as the male, or pollen, parent. The new *Begonia* plant was discovered and selected by the Inventor as a single flowering plant from within the progeny of the stated cross-pollination in a controlled greenhouse environment in Ermelo, The Netherlands in October, 2015.

Asexual reproduction of the new *Begonia* plant by terminal vegetative cuttings taken in a controlled greenhouse environment in Ermelo, The Netherlands since March, 2016 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'KROUTRE01'. These characteristics in combination distinguish 'KROUTRE01' as a new and distinct *Begonia* plant:

1. Broadly upright and mounded plant habit.
2. Moderately vigorous growth habit.
3. Moderately freely branching habit.
4. Dark greyed green-colored leaves.
5. Large single-type red-colored flowers that are positioned above and beyond the foliar plane.
6. Continuous flowering throughout the summer.

Plants of the new *Begonia* differ primarily from plants of the female parent selection in the following characteristics:

1. Plants of the new *Begonia* are larger and more mounding than plants of the female parent selection.
2. Plants of the new *Begonia* have larger flowers than plants of the female parent selection.

Plants of the new *Begonia* differ primarily from plants of the male parent, 'Nonstop Mocca', in the following characteristics:

1. Plants of the new *Begonia* have dark greyed green-colored leaves whereas plants of 'Nonstop Mocca' have bronze-colored leaves.

2. Plants of the new *Begonia* have single-type flowers whereas plants of 'Nonstop Mocca' have double-type flowers.

Plants of the new *Begonia* can be compared to plants of *Begonia boliviensis* x *Begonia* x *tuberhybrida* 'KROUTOR01', disclosed in U.S. Plant Pat. No. 26,248. In side-by-side comparisons conducted in Ermelo, The Netherlands, plants of the new *Begonia* differed primarily from plants of 'KROUTOR01' in flower color as plants of the new *Begonia* have red-colored flowers whereas plants of 'KROUTOR01' have dark orange-colored flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet (FIG. 1 of 2) comprises a side perspective view of a typical plant of 'KROUTRE01' grown in a container.

Figure 2:
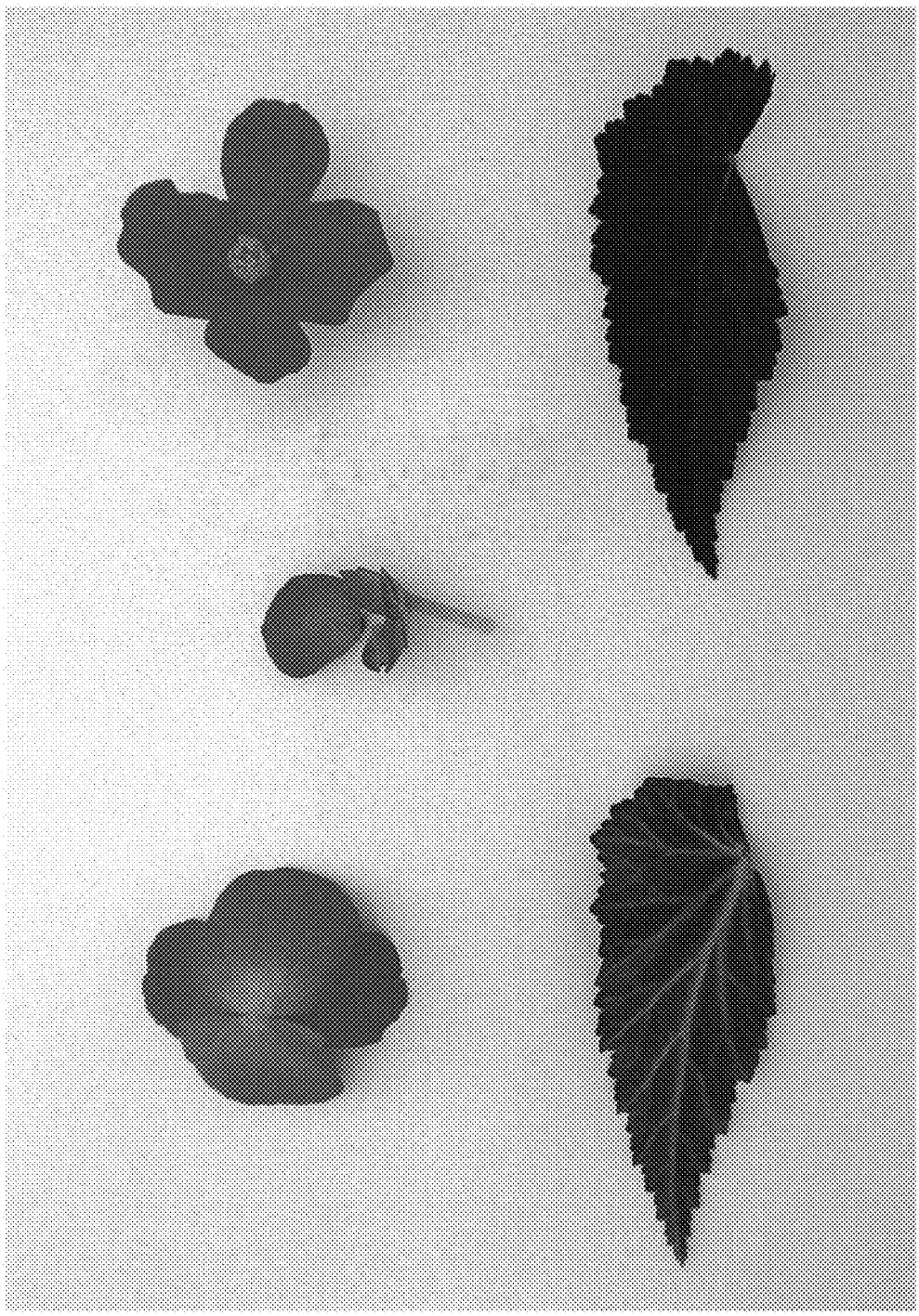

The photograph on the second sheet (FIG. 2 of 2) is a close up view of typical flowers and leaves of 'KROUTRE01'.

DETAILED BOTANICAL DESCRIPTION

The aforementioned photographs and following observations and measurements describe plants grown during the late spring and early summer in 10.5-cm containers in a glass-covered greenhouse in Ermelo, The Netherlands and under cultural practices typical of commercial *Begonia* production. During the production of the plants, day temperatures ranged from 20° C. to 22° C. and night temperatures ranged from 16° C. to 18° C. Plants were three months old when the photographs and description were taken. In the following description, color references are made to The Royal Horticultural Society Colour Chart, 2015 Edition, except where general terms of ordinary dictionary significance are used.

Botanical classification: *Begonia boliviensis* x *Begonia* x *tuberhybrida* 'KROUTRE01'.

Parentage:

*Female, or seed, parent*.—Proprietary selection of *Begonia* x *tuberhybrida* identified as code number KV13H1260-004, not patented.

*Male, or pollen, parent*.—*Begonia* x *tuberhybrida* 'Nonstop Mocca', not patented.

Propagation:

*Type*.—By terminal vegetative cuttings.

*Time to initiate roots, summer and winter*.—About 20 days at temperatures about 20° C.

*Time to produce a rooted young plant, summer and winter*.—About five weeks at temperatures about 20° C.

*Root description*.—Fine, fibrous; typically white to orange brown in color, actual color of the roots is dependent on substrate composition, water quality, fertilizer type and formulation, substrate temperature and physiological age of roots.

*Rooting habit*.—Freely branching; medium density; plants of the new *Begonia* have not been observed to form tubers to date.

Plant description:

*Plant habit and form*.—Broadly upright and mounded plant habit; roughly globular in overall plant shape.

*Growth habit*.—Moderately vigorous growth habit and moderate growth rate; suitable for 9-cm and larger containers; under optimal environmental and cultural conditions, usually about eight weeks are required to produce proportional 10.5-cm potted plants from rooted cuttings.

*Branching habit*.—Moderately freely branching habit, about four basal branches each with about three secondary branches develop per plant; dense and bushy plant habit.

*Plant height, soil level to top of foliar plane*.—About 23.8 cm.

*Plant height, soil level to top of floral plane*.—About 24.7 cm.

*Plant width*.—About 33.3 cm.

*Lateral branches*.—Length: About 10.9 cm. Diameter: About 8 mm. Internode length: About 1.5 cm. Aspect: Erect to about 60° from vertical. Strength: Flexible, bending with the weight of the flowers. Texture and luster: Sparsely pubescent; moderately glossy. Color, developing: Close to 199B. Color, developed: Slightly darker than 146A and 147A; at the internodes, strongly tinged with close to 183B.

*Leaves*.—Arrangement: Alternate; simple. Length: About 14 cm. Width: About 6.2 cm. Shape: Narrowly ovate. Apex: Acute. Base: Oblique, lobes free. Margin: Dentate to crenate; slightly to moderately undulate. Texture and luster, upper surface: Sparsely to moderately pubescent; velvety; slightly glossy. Texture and luster, lower surface: Sparsely to moderately pubescent; slightly velvety; moderately glossy. Venation pattern: Pinnate. Color: Developing leaves, upper surface: Darker than between 138A and N189A. Developing leaves, lower surface: Close to 183A. Fully expanded leaves, upper surface: Darker than N189A with a blackish hue, close to 202A; venation, close to 143A. Fully expanded leaves, lower surface: Close to 183C; venation, close to 146A to 146B. Petioles: Length: About 4.7 cm. Diameter: About 5 mm. Texture and luster, upper and lower surfaces: Moderately pubescent; moderately glossy. Color, upper surface: Close to 185A. Color, lower surface: Close to 199A to 199B. Stipules: Quantity and appearance: Two leafy stipules positioned at base of the leaf. Length: About 9 mm. Width: About 7 mm. Shape: Broadly ovate. Apex: Acute. Base: Broadly cuneate. Margins: Ciliate. Color, upper and lower surfaces: Close to N170D and 174C to 174D; venation, close to 183C.

Flower description:

*Flower form and flowering habit*.—Large single-type rotate flowers arranged in axillary cymes; typically about four flowers per cyme, numerous cymes in flower simultaneously and about 60 flowers developing per plant; flowers face upright to mostly outwardly and are positioned above and beyond the foliar plane.

*Natural flowering season*.—Plants flower continuously from the spring into the autumn in The Netherlands.

*Flower longevity*.—Individual flowers last about ten days on the plant; flowers not persistent.

*Fragrance*.—None detected.

*Inflorescence height*.—About 13 cm.

*Inflorescence diameter*.—About 9.8 cm.

*Flower buds*.—Length: About 2.4 cm. Diameter: Ranging from about 1 cm to 2.3 cm. Shape: Broadly ovate, flattened. Texture and luster: Smooth, glabrous; velvety; matte. Color: Close to 42A, fading towards the base, close to 45C to 45D.

*Female flowers*.—Diameter: About 4.1 cm. Depth: About 2.6 cm. Shape: Rotate. Tepals: Quantity and arrangement: About five arranged in two whorls. Length, inner whorl: About 3.3 cm. Length, outer whorl: About 3 cm. Width, inner and outer whorls: About 2 cm. Shape: Narrowly obovate to obovate. Apex: Obtuse to rounded. Base: Cuneate. Margin: Entire, not undulate. Texture and luster, upper surface: Smooth, glabrous; moderately velvety; matte. Texture and luster, lower surface: Smooth, glabrous; moderately velvety; slightly glossy. Color: When opening, upper surface: Close to between 43A and 46C. When opening, lower surface: Close to 42A and 43A. Fully opened, upper surface: Close to 45B; venation, close to 45B; color does not change with development. Fully opened, lower surface: Close to 43A; venation, close to 43A; color does not change with development. Tepaloids: None observed on female flowers.

*Male flowers*.—Diameter: About 6.5 cm. Depth: About 3.4 cm. Shape: Rotate. Tepals: Quantity and arrangement: About four arranged in two whorls. Length, inner whorl: About 3.9 cm. Length, outer whorl: About 3.8 cm. Width, inner whorl: About 2.7 cm. Width, outer whorl: About 4.4 cm. Shape, inner whorl: Narrowly obovate to obovate. Shape, outer whorl: Reniform. Apex: Obtuse to rounded. Base: Cuneate. Margin: Entire, not undulate. Texture and luster, upper surface: Smooth, glabrous; moderately velvety; matte. Texture and luster, lower surface: Smooth, glabrous; moderately velvety; slightly glossy. Color: When opening, upper surface: Close to between 45B and 46C. When opening, lower surface: Close to 44A. Fully opened, upper surface: Close to 45B; towards the base, close to 42A; venation, similar to lamina; color does not change with development. Fully opened, lower surface: Close to 42A; towards the margins and apex, close to 43A; venation, similar to lamina; color does not change with development. Tepaloids: None observed on male flowers.

*Flower bracts*.—Quantity and arrangement: Two positioned at the top of the peduncle. Length: About 1.3 cm. Width: About 1.9 cm. Shape: Reniform. Apex: Obtuse to rounded. Base: Broadly cuneate. Margin: Finely ciliate. Texture and luster, upper and lower surfaces: Smooth, glabrous; slightly glossy. Color, upper surface: Close to 42A and 42B; towards the base, close to 144C. Color, lower surface: Close to N45B and N45C; towards the base, close to 144C.

*Peduncles*.—Length: About 6.8 cm. Diameter: About 4 mm. Angle: About 50° from lateral branch axis. Strength: Flexible, bending with the weight of the flowers. Texture and luster: Smooth, glabrous; moderately glossy. Color, upper and lower surfaces: Close to 152B; proximally tinged with close to 185A.

*Pedicels*.—Length: About 2.8 cm. Diameter: About 3 mm. Angle: About 40° from peduncle axis. Strength: Flexible, bending with the weight of the flowers. Texture and luster: Smooth, glabrous; glossy. Color, upper surface: Close to 147D, variably tinged with close to N45B. Color, lower surface: Close to 147D, variably tinged with close to 42B.

*Reproductive organs*.—Stamens (present on male flowers only): Quantity per flower: About 60. Filament length: About 6 mm. Filament color: Close to 8B. Anther shape: Obovate; basifixed. Anther length: About 1 mm. Anther color: Close to 14A. Pollen amount: Scarce. Pollen color: Close to 4D. Pistils (present on female flowers only): Quantity per flower: About six, fused in pairs. Pistil length: About 7 mm. Style length: About 6 mm. Style color: Close to 33B. Stigma color: Close to 22A. Ovary color: Close to 144B; apex, close to 45C.

*Seeds and fruits*.—To date, seed and fruit development have not been observed on plants of the new *Begonia*.

Disease & pest resistance: To date, resistance to pathogens and pests common to *Begonia* plants has not been observed on plants of the new *Begonia*.

Temperature tolerance: Plants of the new *Begonia* have been observed to tolerate high temperatures about 35° C. and to be suitable for USDA Hardiness Zones 10 to 12.

It is claimed:

1. A new and distinct *Begonia* plant named 'KROUTRE01' as illustrated and described.

* * * * *